United States Patent
Li et al.

(10) Patent No.: US 8,731,268 B2
(45) Date of Patent: May 20, 2014

(54) CT DEVICE AND METHOD BASED ON MOTION COMPENSATION

(75) Inventors: Liang Li, Beijing (CN); Zhiqiang Chen, Beijing (CN); Li Zhang, Beijing (CN); Kejun Kang, Beijing (CN); Yuanjing Li, Beijing (CN); Ziran Zhao, Beijing (CN); Yinong Liu, Beijing (CN); Yuxiang Xing, Beijing (CN); Xin Jin, Beijing (CN)

(73) Assignees: Tsinghua University (CN); Nuctech Company Limited (CN)

( * ) Notice: Subject to any disclaimer, the term of this patent is extended or adjusted under 35 U.S.C. 154(b) by 7 days.

(21) Appl. No.: 13/142,725

(22) PCT Filed: Dec. 27, 2010

(86) PCT No.: PCT/CN2010/080312
§ 371 (c)(1),
(2), (4) Date: Jun. 29, 2011

(87) PCT Pub. No.: WO2011/097927
PCT Pub. Date: Aug. 18, 2011

(65) Prior Publication Data
US 2012/0014579 A1    Jan. 19, 2012

(30) Foreign Application Priority Data
Feb. 10, 2010 (CN) .......................... 2010 1 0111359

(51) Int. Cl.
*G06K 9/00* (2006.01)
(52) U.S. Cl.
USPC .......................................... 382/131; 382/154
(58) Field of Classification Search
None
See application file for complete search history.

(56) References Cited

U.S. PATENT DOCUMENTS

| 5,287,276 | A    | 2/1994  | Crawford et al. |         |
|-----------|------|---------|-----------------|---------|
| 6,236,705 | B1   | 5/2001  | Stergiopoulos et al. |    |
| 6,662,036 | B2 * | 12/2003 | Cosman          | 600/411 |
| 8,073,528 | B2 * | 12/2011 | Zhao et al.     | 600/424 |

(Continued)

FOREIGN PATENT DOCUMENTS

| CN | 101501730 A   | 8/2009  |
|----|---------------|---------|
| JP | 2009-273672 A | 11/2009 |

OTHER PUBLICATIONS

"International Application Serial No. PCT/CN2010/080312, International Search Report mailed Apr. 7, 2011", 6 pgs.

(Continued)

*Primary Examiner* — Stephen R Koziol
*Assistant Examiner* — Sean Conner
(74) *Attorney, Agent, or Firm* — Schwegman Lundberg & Woessner, P.A.

(57) ABSTRACT

A CT device and method based on motion compensation are proposed. The present invention obtains motion parameters of a target object by using a stereo-vision-based motion measurement system, and then implements motion compensation through the technology based on reconstructed image matrix transformation, thereby obtaining a clear 2D/3D CT image while eliminating motion artifacts. The present invention can effectively eliminate motion artifacts caused by the scanned object's own motions in the CT scanning, and can be easily embedded into the existing CT scanning equipments. The present invention can improve quality of the CT images, and is especially important for CT imaging of some special groups of people that can not control their own motions, such as Parkinson's patients, infants, living mouse and so on. It can also improve ultra-high-resolution imaging of human body.

11 Claims, 6 Drawing Sheets

(56) References Cited

U.S. PATENT DOCUMENTS

| | | |
|---|---|---|
| 2008/0219534 A1* | 9/2008 | Faul et al. .................... 382/131 |
| 2008/0287772 A1* | 11/2008 | Declerck et al. ............. 600/411 |
| 2008/0317313 A1* | 12/2008 | Goddard et al. ............. 382/131 |
| 2009/0103792 A1* | 4/2009 | Rahn et al. ................... 382/131 |
| 2009/0209846 A1* | 8/2009 | Bammer ....................... 600/421 |
| 2009/0245457 A1* | 10/2009 | Takeuchi et al. ................. 378/8 |
| 2009/0262996 A1* | 10/2009 | Samsonov et al. ........... 382/130 |
| 2010/0014732 A1* | 1/2010 | Vija et al. .................... 382/131 |
| 2010/0208962 A1 | 8/2010 | Roessl et al. |
| 2011/0123081 A1* | 5/2011 | Sebok et al. .................. 382/131 |
| 2011/0142316 A1* | 6/2011 | Wang et al. ................... 382/131 |
| 2012/0106814 A1* | 5/2012 | Gleason et al. ............... 382/131 |
| 2012/0141007 A1* | 6/2012 | Takizawa et al. ............. 382/131 |

OTHER PUBLICATIONS

"International Application Serial No. PCT/CN2010/080312, Written Opinion mailed Apr. 7, 2011", 4 pgs.

* cited by examiner

CT DEVICE AND METHOD BASED ON MOTION COMPENSATION

CROSS-REFERENCE TO RELATED APPLICATIONS

This application is a nationalization under 35 U.S.C. §371 of International Application No. PCT/CN2010/080312, filed on Dec. 27, 2010 and published as WO2011/097927, on Aug. 18, 2011, which claims priority under 35 U.S.C. §119 to Chinese Application No. 201010111359.8, filed Feb. 10, 2010, the entire contents of which are incorporated herein by reference in their entirety.

FIELD OF INVENTION

The present invention relates to radiography imaging, in particular to a CT (Computerized Tomography) device and method based on motion compensation.

BACKGROUND OF THE INVENTION

Since 1972, Hounsfield invented the first CT machine, CT technology has brought a revolutionary impact to medical diagnosis and nondestructive testing in industry and CT has become one important means of detection in the medical, biotechnology, aerospace and defense sectors and the like industries. As technology advances, scan modes and imaging methods for CT are continually improving, 3D cone-beam CT has become the mainstream of research and application. X-ray cone-beam CT has been widely used in clinical, safety inspection, NDT (Non-Destructive Test) and other fields. Especially in clinical diagnosis, helical CT has become an indispensable means of inspection.

In 1989, spiral CT was put into clinical practices. Due to the advantages of spiral CT, it has gradually replaced the previous plane CT. Compared with plane CT, spiral CT has the following advantages: spiral CT can uninterruptedly collect projection data and get 3D volume data of an object through a specifically designed reconstruction algorithm so as to significantly shorten the time for CT scanning, improve the Z-axis resolution of a reconstructed image and reduce motion artifacts. In 1991, the company, Elscint, firstly introduced the double slice CT on basis of the single slice CT, hence opening a prelude to the rapid development of Multi-slice spiral CT (i.e., Multi-slice CT, MSCT).

MSCT differs from the single slice spiral CT in that the detectors of the single slice CT are arranged in a single row and can collect only one slice of fan-beam projection data at a time, while MSCT has a multi-row arrangement of detectors and thus can simultaneously collect several slices of cone-beam projection data. Thus, compared with the single slice spiral CT, MSCT has been greatly enhanced in performance, specifically with the coverage of X-ray beam being greatly increased, the utilization of X-ray being effectively improved and the scanning time being shortened. This leads to 3D reconstructed images with higher quality. In 1998, companies, such as GE, Siemens, Toshiba and Philips, introduced a 4-slice spiral CT, hence opening a prelude to fierce competitions among these major medical device companies. In 2001, GE pioneered an 8-slice spiral CT. In 2002, GE, Siemens, Toshiba and Philips respectively launched a 16-slice spiral CT. In 2005, Toshiba introduced the 256-slice spiral CT. In 2007, in the 93rd conference of the North American radiology in Chicago, US, Toshiba announced the launch of its new 320-slice spiral CT products. The Siemens launched in 2005 the first dual-energy spiral CT. The scanning speed of the latest MSCT has been up to 4 turns per second, and has been widely used in 3D imaging for human body, angiography, cardiac imaging, perfusion imaging and the like. On basis of MSCT technology, new technologies like computer-aided surgery, virtual endoscopy and radiotherapy have been emerged and developed.

Although CT technology has achieved great successes in industry, security, medical and other fields, due to complexity and diversity of engineering application conditions, higher requirements poses a need for further development of CT technology. During CT scanning, motions of the scanned object frequently occur, especially in CT imaging of living bodies. For example, during medical CT scanning, due to the inherent motions of organs, there are often motion artifacts in CT images, leading to image blurring, ghosting, etc., which may affect the accuracy of physician's diagnosis of diseases. There are a variety of physiological motions for human organs in the normal metabolism course, including: heart beating, lungs breathing exercises, pulses, gastrointestinal motility and the like. Among the motions of these organs, except for breathing may be controlled by holding one's breath, it is difficult to temporarily stop most of the other motions. In addition, for some special sections of population that are unable to control their own body movements, such as Parkinson's patients, infants, mental patients without self-control and the like, noticeable limb movements may occur during CT scanning. These movements inevitably lead to motion artifacts in MSCT image, poor picture quality, and even a failed scanning. Therefore, studies on reduction and elimination of motion artifacts are of great significance for CT imaging.

In the case of holding one's breath, a healthy human body has an average movement displacement of about 0.35 mm in 10 seconds, which may not lead to serious motion artifacts in the image since the current MSCT image has a resolution of only 0.4 mm. However, the organs in a human's torso are influenced by heart beat, gastrointestinal peristalsis and the like. These organs have more obvious movements than that of the head. Especially for patients, since their ability to control their bodies have been weakened, the range of movement may be more than 1 mm or even more, thereby leading to severe motion artifacts while affecting quality of CT images.

A fundamental way to reduce motion artifacts is to improve imaging speed so as to reduce the impact caused by organ motions in the scanning process. However, the existing MSCT enables X-ray machines and detectors to rapidly rotate around the body through the slip ring technology, so as to carry out the CT scanning. Currently, the highest scanning speed is 0.25 second/circle. Due to a variety of restrictions such as centrifugal force, material strength and the like, this speed has already achieve the uppermost limit in industry applications, and thus it is difficult to enable a breakthrough in next few years. In addition to MSCT, speeds for other medical CT and industrial CT scanning are far lower than 0.25 seconds/circle. Thus, it is impossible to eliminate motion artifacts by simply increasing the scanning speed.

Another existing technology for suppressing motion artifacts is Gating technology, which has been applied in cardiac imaging. The Gating technology groups MSCT scanning data in accordance with the heart phases, performs image reconstruction for the groups, respectively, and then gets a final CT image by using image fusion technology. The problems with Gating technology are that some X-ray projection data are not effectively used, leading to an increased radiation dose used in cardiac imaging. Medical radiation has become the topmost man-made ionizing radiation, and reduction of X-ray dose in CT inspection is a major issue related to health of the public and future generations.

SUMMARY OF THE INVENTION

It is an object of the present invention to provide a CT device and method based on motion compensation, which measures motion coordinates of a scanned object by using a stereo vision system and then eliminates motion artifacts in a CT image by using a motion compensation technique based on matrix transformation of an reconstructed image, thereby obtaining a CT image of high quality.

In an aspect of the present invention, a CT (Computerized Tomography) device based on motion compensation, comprising: a CT scanning device adapted to perform CT scanning on a scanned object; a stereo vision measurement system adapted to measure a motion parameter of the scanned object in synchronization with the scanning of the CT scanning device; and an imaging device adapted to compensate for the motion of the scanned object during the CT scanning by performing a transformation on a reconstructed image matrix based on the motion parameter.

According to an embodiment of the present application, the stereo vision measurement system comprises a first camera and a second camera adapted to collect a 2D/3D image of the scanned object in synchronizations with the scanning of the CT scanning device, and the imaging device calculates the motion parameter of the scanned object based on the collected 2D/3D image.

According to an embodiment of the present application, the synchronizations of the first and second cameras with the CT scanning device are based on collection timing of a detector in the CT scanning device.

According to an embodiment of the present application, a period of a synchronous collection pulse trigger signal is adjusted to an integer multiple of the detector collection period, as collection triggers for the first and second cameras, when a detector collection rate used in the CT scanning device is higher than collection rates of the first and second cameras.

According to an embodiment of the present application, when performing CT reconstruction, 3D coordinates and motion parameter of the scanned object are obtained in correspondence to CT projections by interpolation.

According to an embodiment of the present application, a detector collection signal is used as a synchronous trigger signal for the first and second cameras for image collection, when the detector collection rate used in the CT scanning device is lower than or equal to the collection rates of the first and second cameras.

According to an embodiment of the present application, the imaging device performs a respective matrix transformation on the reconstructed image matrix based on the measured motion parameter before each back projection, so as to make the image matrix keep consistent with the pattern of the object at every moment.

According to an embodiment of the present application, the motion parameter includes at least a part of rotation and translation of the scanned object.

According to an embodiment of the present application, the compensation for the motion is implemented in FBP and ART algorithms.

In another aspect of the present invention, a method for use in a CT device, comprising: performing CT scanning on a scanned object with a CT scanning device; measuring a motion parameter of the scanned object in synchronization with the scanning of the CT scanning device; and compensating for the motion of the scanned object during the CT scanning by performing a transformation on a reconstructed image matrix based on the motion parameter.

The device according to the embodiments of the present invention can be embedded as a separate module into the exiting or newly developed CT devices. With the device and method according to the embodiment of the present invention, a CT image can be obtained in which motion artifacts caused by motions of the object during the CT scanning are effectively eliminated.

BRIEF DESCRIPTION OF THE DRAWINGS

The above advantages and features of the present invention will be apparent from the following detailed description taken conjunction with the drawings in which:

FIG. 4 shows a timing diagram of controlling synchronous collection by an X-ray detector and a camera, in which FIG. 4(a) shows a timing diagram when a collection rate of a detector used in a CT system is higher than that of the camera, FIG. 4(b) shows a timing diagram when a collection rate of the detector used in the CT system is equal to that of the camera, and FIG. 4(c) shows a timing diagram when a collection rate of the detector used in the CT system is lower than that of the camera;

FIG. 6(a) shows a model at an initial time, and FIG. 6(b) shows a changed model after a period of time;

FIG. 7(a) shows a conventional FBP reconstruction result, FIG. 7(c) shows a motion-compensated FBP reconstruction result using the present invention, FIGS. 7(b) and (d) show a horizontal center section line and a vertical center section line in the reconstruction result, respectively, FIG. 7(e) shows a conventional ART reconstruction result, FIG. 7(g) shows a motion-compensated ART reconstruction result using the present invention, and FIGS. 7(f) and (h) show a horizontal center section line and a vertical center section line in the reconstruction result, respectively.

DETAILED DESCRIPTION OF THE PREFERRED EMBODIMENTS

Now, a detailed description will be given to the preferred embodiments of the present invention with reference to the figures, throughout which like reference signs denote identical or similar component, though illustrated in different figures. For clarity and conciseness, specific description of some known functions or structures incorporated here will be omitted otherwise the subject of the present invention may be obscured.

Figure 1:
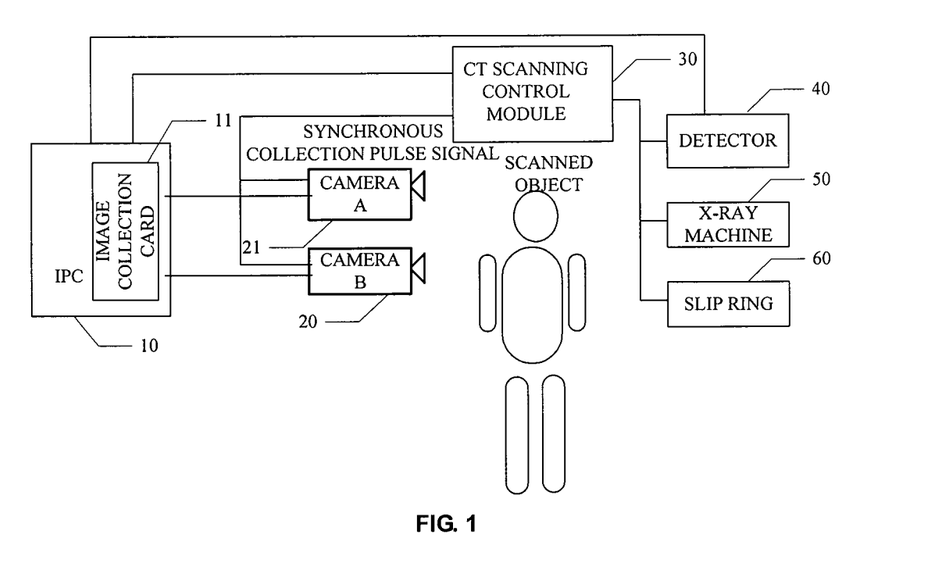
FIG. 1 is a schematic block diagram illustrating a CT device based on motion compensation according to an embodiment of the present invention.

According to an embodiment of the present invention, a CT device and a method thereof based on motion compensation are proposed. FIG. 1 shows a schematic block diagram of a CT device based on motion compensation according to the embodiment of the present invention.

As show in FIG. 1, the CT device according to the present embodiment is equipped with a stereo vision system. During the CT scanning, motions of a scanned object are also collected by an image collection card 11 under the control of a CT scanning control module 30. Motion parameters of the object are calculated by using camera A 20 and camera B 21 in cooperation with an algorithm stored in a memory (not shown) of an IPC (Industrial Personal Computer) 10. Thereafter, during an image reconstruction process, the motions are compensated based on the calculated motion parameters to eliminate motion artifacts.

As shown in FIG. 1, the device according to the embodiment of the present invention is further provided with an X-ray machine 50, a detector 40 and a slip ring 60 for CT scanning. During the CT scanning, the scanned object placed between the X-ray machine 50 and the detector 40 may have motions of some body parts, such as head.

According to the present embodiment, 2D optical images of the scanned object are synchronously collected during the CT scanning by a stereo vision system. 3D coordinates of the scanned object corresponding to each CT projection are recorded with a fast binocular-/trinocular-based 3D coordinate calibration algorithm. Then the motion compensation is performed with reconstructed image matrix transformation in the CT reconstruction process, using the measured motion parameters of the scanned object. In this way, motion artifacts in the finally reconstructed 2D/3D images can be eliminated, and a CT image of high accuracy can be obtained.

As a method for reconstructing a 3D image from multiple 2D images by using a computer, stereo vision has been an important research aspect in the computer vision research field, and a large number of research contributions have been achieved especially in the last two decades. Stereo vision is mainly divided into two stereo measurement technologies, i.e. passive and active. In the former one, illumination for an object is provided by lighting surrounding the object. In the latter one, a dedicated light source device is used for providing illumination around the object. The camera-based stereo vision measurement technology is mostly applied, which may be further divided into monocular, binocular, and multi-nocular modes depending on the number of cameras in use. The binocular technology for performing stereo vision measurement by using two cameras, which will be detailed in the following, is a fast dual-view-based 3D-coordinate positioning method. The stereo vision technology used in measuring 3D coordinates of motions is not limited to binocular stereo vision. To those skilled in the art, the above binocular/trinocular 3D coordinate calibration algorithms can be replaced by other algorithms, such as those used in stereo vision systems adopted to collect 3D coordinates and motion parameters of a scanned object in synchronization with CT scanning.

Binocular stereo vision is an important branch of computer vision, in which two images of a single motion scene is picked up by two cameras located at different positions, and a 3D coordinate value of a spatial point by calculating the parallax of the two corresponding points in the two images. In the 1980s, Marr (in MIT) proposed a vision calculation theory and applied it in binocular matching, so that two plane images with a parallax can produce a stereo image having a depth. This established the theoretical foundation for the development of binocular stereo vision. Compared with other stereo vision methods, the binocular stereo vision method can directly simulates human eyes in term of processing scenes, and is more simple and reliable. The binocular stereo vision method has been applied in many fields, such as industrial non-contact measurement, robot navigation and aerial survey, 3D surveying, and virtual reality.

Figure 3:
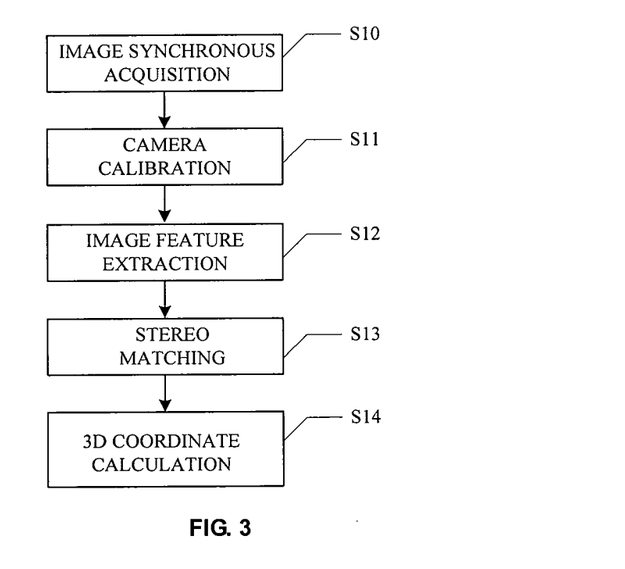
FIG. 3 is a schematic flowchart depicting a process for performing a 3D coordinate measurement using a stereo vision system.

As shown in FIG. 3, the binocular stereo vision method can be implemented in the following steps: an image acquisition step S10, a camera calibration step S11, a feature extraction step S12, an image matching step S13 and a 3D coordinate calculation step S14.

According to an embodiment of the present invention, with respect to a CT scanning environment and characteristics of a target object's motions, a binocular stereo vision measurement system and method for CT imaging are proposed. Then, accurate CT imaging can be achieved by using a matrix transformation of a reconstructed image as described later to eliminate motion artifacts.

According to an embodiment of the present invention, a stereo vision measurement system is used to measure 3D coordinates of a scanned object while being scanned with an X-ray source, to obtain a motion parameter of the object. Then, the proposed motion compensation is used to eliminate motion artifacts to get a clear CT image. On basis of the binocular stereo vision theory, the stereo vision measurement system according to the present embodiment observes a single object from viewpoints at different positions to acquire images of the CT scanned object at different views, and acquires 3D coordinate information of the object by calculating a positional deviation (i.e. parallax) between corresponding pixels of the images with geometrical imaging theory.

As shown in FIG. 1, the stereo vision measurement system mainly comprises components: two cameras 20, 21 having the same performance parameters, an image collection card 11, and auxiliary devices like data transmission lines. Two images of the scanned object are simultaneously obtained from two different views, and then the 3D coordinates of the scanned object are calculated. As shown in FIG. 1, two cameras A and B are fixedly arranged at a distance from each other. Typically, CCD cameras may be used. Each of the two cameras is connected to a computer 10 through the video collection card 11 for transferring data to the computer 10. In the computer 10, a motion-compensated image reconstruction process may be performed by executing software programs. Generally, a stereo vision system may require just two cameras for synchronous collection. However, in the embodiment of the present invention camera 20 and camera 21 are required for not only synchronous collection but also for a collection in synchronization with the collection of a detector 40 in the CT scanning system, so that 3D coordinates of the scanned object (calculation for which will be described in the following) can correspond to the collected CT projection data, thereby facilitating CT motion-compensated reconstruction. Therefore, in order to enable synchronous collection of the two cameras with the CT scanning system, a collection pulse signal may be derived from the CT scanning control module 30, as an external trigger source for achieving collection of camera 20 and camera 21 synchronized with the CT detector 40.

Figure 2:
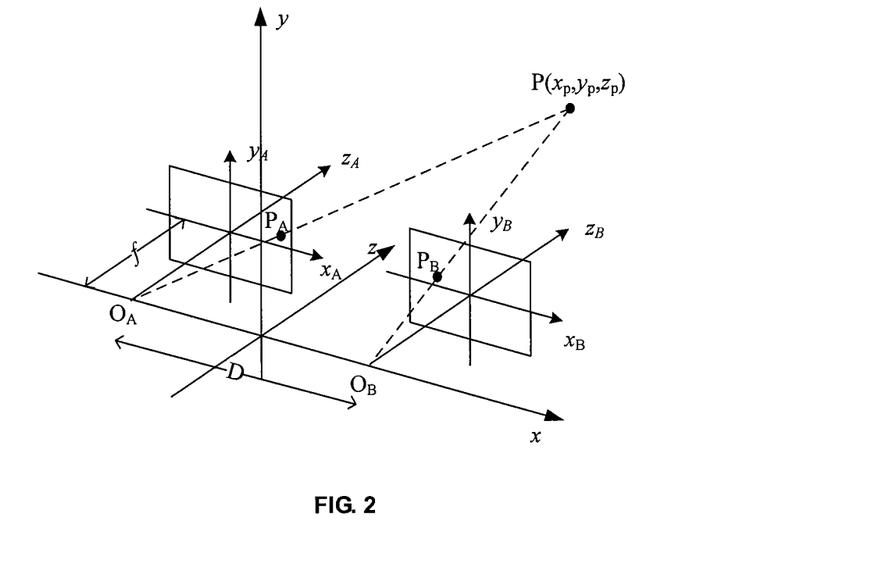
FIG. 2 is a schematic diagram showing relative positions and coordinates of two cameras in a binocular stereo vision system.

To facilitate calculation of the object's 3D coordinates, the positions of two cameras A and B are generally fixed to each other, as shown in FIG. 2. Firstly, a Cartesian coordinate system xyz is defined for a 3D space where the scanned object is located. Then, imaging planes of the cameras A and B are defined as $x_A y_A$ and $x_B y_B$, respectively. Since the performance parameters of the two cameras are exactly the same, the optical axes $z_A$ and $z_B$ of the imaging planes can be in parallel, while the imaging planes $x_A y_A$ and $x_B y_B$ can be in the same plane, with their horizontal axes $x_A$ and $x_B$ completely coinciding with x-axis of the 3D spatial coordinate system. $P_A$ and $P_B$ respectively indicate points where an object point P is imaged in the imaging planes of the cameras A and B. $O_A$ and $O_B$ respectively indicate focuses of the cameras A and B, and are symmetrical on the x-axis with respect to the origin of coordinate. Distances from the focuses to the imaging planes, i.e. focal lengths f, depend on the cameras' hardware and thus can be considered as known. The distance between the two cameras is D, which may be obtained with measurement.

The 3D coordinates of the object point P in the space may be labeled as ($x_p$, $y_p$, $z_p$). At a time moment when the two cameras A and B simultaneously capture images of the point P, the corresponding 3D coordinates may be respectively labeled as $P_A=(x_{pA}, y_{pA})$ and $P_B=(x_{pB}, y_{pB})$ in respective imaging planes. Since the images by the cameras A and B are in the same plane and their x-axes coincide, image points of the point P with respect to the cameras A and B have the same y coordinate, that is $y_{pA}=y_{pB}$. The following can be obtained from a triangular geometric relationship:

$$\begin{cases} x_{pA} = f \cdot \frac{x_p + D/2}{z_p} \\ x_{pB} = f \cdot \frac{x_p - D/2}{z_p} \\ y_{pA} = y_{pB} = f \cdot \frac{y_p}{z_p} \end{cases} \quad (1)$$

The 3D coordinates of the object point P may be calculated by solving the above equation set:

$$\begin{cases} x_p = \frac{D}{2} \cdot \frac{x_{pA} + x_{pB}}{x_{pA} - x_{pB}} \\ y_p = \frac{y_{pA} \cdot D}{x_{pA} - x_{pB}} \\ z_p = \frac{f \cdot D}{x_{pA} - x_{pB}} \end{cases} \quad (2)$$

So, 3D spatial coordinates of any point of the object may be calculated by using two images captured by two cameras 20 and 21, which are located on the left and right and synchronized. The above algorithm involves only point-to-point operation. Thus, the corresponding 3D coordinate may be calculated by using the above algorithm, as long as matching points of the point P can be found in the images captured by the two cameras. The processes of binocular-based stereo vision measurement and 3D coordinate calculation are fulfilled by the following method.

As shown in FIG. 3, at step S10, the two cameras perform synchronous image capturing, which is the basis for 3D coordinate computation. When the cameras are arranged as shown in FIG. 1, the cameras 20 and 21 simultaneously capture 2D images of a target object in accordance with a synchronous collection pulse signal outputted from the CT scanning control module 30, and transfer the 2D images to the computer 10 through the image collection card 11 while recording time moments for collecting the image data.

The computer stereo vision imaging typically adopts binocular imaging technique, and sometimes also adopts tri-nocular or multi-nocular imaging technologies. Since the CT scanned objects, such as human body and wrapped luggage, are is generally stationary, a stereo vision system with two cameras can meet the requirements of practical applications.

At step S11, camera calibration is performed. The camera calibration is intended to accurately determine the positions and property parameters of the cameras and to establish an imaging model. Therefore, correspondence between an object point in the spatial coordinate system and its image point in an imaging plane can be determined, i.e. determination of a transformation matrix. In general, the correspondence depends on the geometric model of the camera. Although some parameters, such as the distance between two cameras, the focal lengths of the cameras and etc., can be obtained by measuring or reading introduction of the camera parameters, it is required to experimentally measure and calculate these parameters, i.e. camera calibration, in order to more accurately determine these parameters. Therefore, the camera calibration is intended to determine the internal geometric and optical characteristics (i.e. intrinsic parameters) of the cameras as well as 3D coordinate positions and orientations of the cameras with respect to the World coordinate system (i.e. extrinsic parameters). In order to more accurately determine these parameters, there are generally about 10 markers set in an experiment, and the 3D coordinates of these markers are known in the World coordinate system. All of the above parameters are determined by measuring coordinates of the 10 markers in the imaging coordinate system of the camera. As such, the camera calibration is completed.

At step S12, image feature extraction is performed. The image feature extraction is to obtain image features for subsequent matching. The matching features may mainly include dot feature, line feature, area feature and the like. Determination as to extract which feature depends on actual scanned object. For example, for metal parts, precision instruments and the like, line features are generally extracted; for luggage, area features are generally extracted. Some objects do not have distinctive features. For example, when imaging the stomach part of a human body using medical CT devices, an auxiliary marker is generally pasted on the surface of the body part, such as a pattern of the Chinese character "田" having white and black colors alternated. It should be noted that since a 2D image collected by a camera often contains a variety of random noises and distortions, it is necessary to pre-process the image before feature extraction, so as to emphasize useful information, suppress useless information, improving image definition and quality while facilitating computer processing of the image for feature analysis and extractions.

At step S13, stereo matching is performed. The stereo matching is to find correspondence between image features in two images simultaneously captured by two cameras. For a single object, its images captured from different viewpoints may be different. With the correspondence between the matching features, a matching relationship is established between the two images.

At step S14, 3D coordinates are calculated. After determining the matching relationship, information on 3D coordinates of these feature points may be determined by using the equation (2), so as to further obtain 3D motion parameters of the object's respective feature points.

As noted above, image collections of the cameras 20 and 21 shall be synchronized with scanning of the CT scanning system. The synchronized collection may ensure that the two cameras can achieve collection synchronous with the detectors of the CT system. Since the cameras and X-ray detector usually have different collection rates, it is necessary to specifically design timing control. Detectors used in different CT systems usually have different collection rates. For example, as the mainstream product currently used in hospitals, MSCT's detector has a collection rate up to about 1000 Hz, while some cone-beam CT systems use plane detectors with a collection rate of only 1 to 30 Hz. A camera typically has an image capture rate of 25 or 30 Hz, and a high-speed camera may achieve a rate up to 100 Hz or even higher. During the synchronous collection, it is needed to design different synchronous timings based on different collection frequencies.

Figure 4:
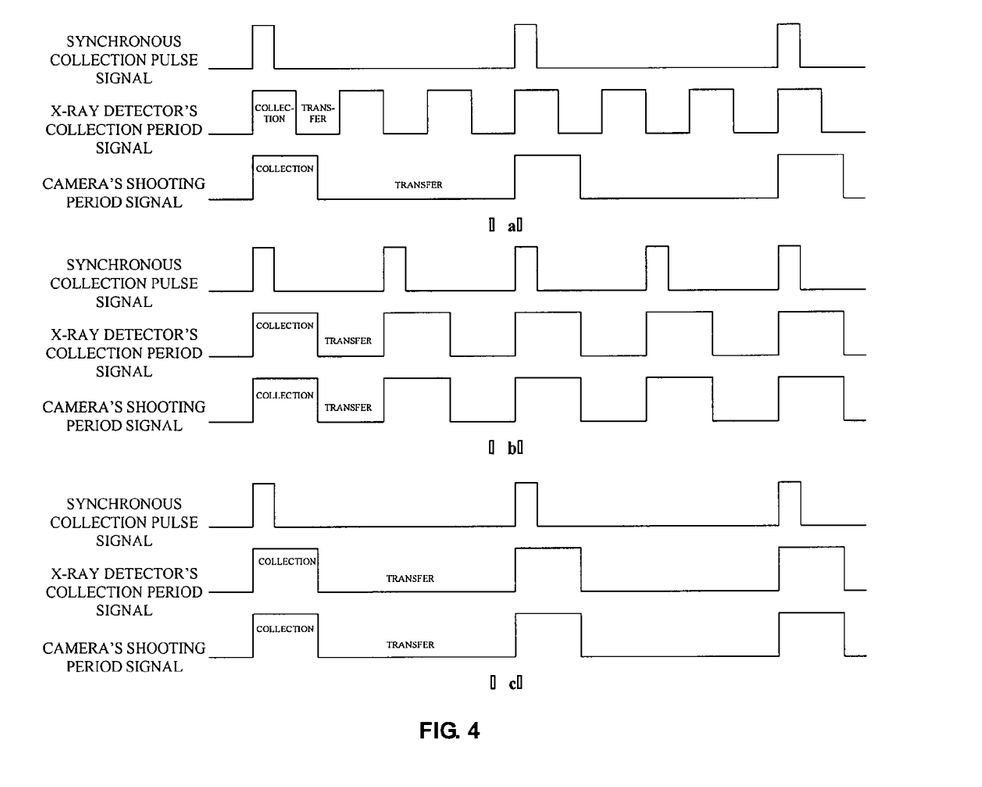

As shown in FIG. 4, there are the following three options: (1) when the collection rate of the detector used in the CT system is higher than that of the camera, the timing as depicted in FIG. 4(a) may be adopted, and a period of a synchronous collection pulse trigger signal may be adjusted to be an integer multiple of the X-ray detector 40's collection period, as collection triggers for the cameras 20 and 21; the number of the object's images captured by the cameras 20 and 11 is less than the number of the CT scanned projections, and it is needed to perform interpolation in the following motion-compensated CT reconstruction, so as to get 3D coordinates corresponding to the CT projections one by one; (2) when the collection rate of the detector 40 used in the CT system is the same with those of the cameras, the timing as depicted in FIG. 4(b) may be adopted; the CT projections corresponds to the images of the cameras one by one; and (3) when the collection rate of the detector 40 used in the CT system is lower than those of the cameras 20 and 21, the timing as depicted in FIG. 4(c) may be adopted, and the collection signal of the X-ray detector 40 may be used as a signal for triggering a synchronization between the cameras 20 and 21 for image collection; the images of the cameras also correspond to the CT projections one by one.

3D coordinates of the object during the CT scanning may be calculated through the stereo vision measurement, and then images of a moving object may be reconstructed by utilizing an image matrix transformation-based CT reconstruction algorithm, which will be described in the following, to obtain a CT image with motion artifacts eliminated.

In case motions of an object during the CT scanning are known, the CT reconstruction may be performed with the reconstruction method according to the embodiment of the present invention. It shall be noted that, for the method according to the embodiment of the present invention, the type of motions that can be taken by the object is limited. Particularly, it is required that the object's motion can be divided into rigid motions of some small units into which the object is divided, that is, the motion of the scanned object can be regarded as rigid motions taken by the respective small units independent from each other. Actually, most objects in real life may be considered as taking such type of motion, such as vibration of metal parts, heart beating, slight swing of human head, and the like. Therefore, the CT image reconstruction method proposed in this embodiment may satisfy the requirement for eliminating most motion artifacts encountered by the practical CT applications. When the scanned object takes rigid motion as a whole, this may be regarded as a special form in which all of the small units of the object take the motion together. Therefore, the method according to the embodiment of the present invention will be described in the following in such a general case that all of the small units of the object respectively take rigid motions.

It shall be further noted that since the reconstruction method is independent of the specific form of the CT scanning, that is, the method may be used either in plane-beam CT image reconstruction, or in fan-beam or cone-beam CT image reconstruction. Therefore, for a clear illustration, the method will be explained in detail by taking plane beams as an example.

Firstly, projection of plane beams in a 2D plane may be expressed by the following equation:

$$p(\hat{\theta},s) = \int_{R^2} f(\vec{x}) \delta(\vec{x} \cdot \hat{\theta} - s) d\vec{x} \quad (3)$$

wherein $f(\vec{x})$ is a function expression of the scanned object, $\theta$ is a unit directional vector perpendicular to the projection direction, and s is a projection position where an X-ray is projected onto the detector. As the algorithm most widely applied in the CP image reconstruction, FBP (Filter-Back-Project) algorithm requires that the projection data shall be firstly filtered as follows:

$$g(\hat{\theta},s) = \int_{-s_0}^{s_0} p(\hat{\theta},s') \cdot h(s-s') ds' \quad (4)$$

wherein h(s) is a filtering function, which generally adopts Ramp filter. Then, back-projection may be performed on the filtered projection data, so as to reconstruct $f(\vec{x})$. The back projection formula may be as follows:

$$f(\vec{x}) = \int_{\theta} g(\hat{\theta},s) \delta(\vec{x} \cdot \hat{\theta} - s) d\hat{\theta} \quad (5)$$

Equation (5) is the FBP reconstruction algorithm that most traditional CT uses. When there are motions of the object in the CT scanning process, the X-ray detector records projection data of the object in its movement. At this time, $f(\vec{x})$ obtained by reconstruction using the above FBP algorithm mixes different motion patterns of the object during the CT scanning. Therefore, the reconstructed image has motion artifacts, resulting in a reduced image quality. In order to eliminate motion artifacts in the reconstruction process, a multi-body rigid motion model is firstly defined as follows: the scanned object may be divided into several small units, each unit taking individual rigid motions. The rigid motion of a single unit may be expressed by the following equation:

$$f_t(\vec{x}) = f\left(\begin{bmatrix} \cos(\varphi(t)) & \sin(\varphi(t)) \\ -\sin(\varphi(t)) & \cos(\varphi(t)) \end{bmatrix} \vec{x} + \vec{A}(t)\right) \quad (6)$$

In the above equation, the rigid motion is decomposed into two motions: rotation motion and translation motion. φ(t) indicates an angle that each unit of the object has rotated at time t in rotation motion, and $\vec{A}(t)$ indicates a translation motion vector of the object in translation motion. The definition is as follows:

$$\Gamma_t(\vec{x}) = \begin{bmatrix} \cos(\varphi(t)) & -\sin(\varphi(t)) \\ \sin(\varphi(t)) & \cos(\varphi(t)) \end{bmatrix} \vec{x} + \vec{A}(t) \quad (7)$$

The above equation is substituted into the equation (6), and then the following equation may be obtained:

$$f_t(\vec{x}) = f(\Gamma_t(\vec{x})) \quad (8)$$

For all the units of the object, accumulation is performed. Then, a motion expression of the whole object may be obtained:

$$f_t(x) = \Sigma_i f_{t,i}(\vec{x}) \quad (9)$$

wherein $f_{t,i}(\vec{x})$ denotes a distribution function of the i$^{th}$ unit of the object at time t.

When there are multi-body motions of the object, projection of plane beams may become:

$$p_t(\hat{\theta}, s) = \int_{R^2} \sum_i f_{t,i}(\vec{x})\delta(\vec{x}\cdot\hat{\theta}-s)d\vec{x} \qquad (10)$$

$$= \sum_i \int_{R^2} f_{t,i}(\vec{x})\delta(\vec{x}\cdot\hat{\theta}-s)d\vec{x}$$

$$= \sum_i p_{t,i}(\hat{\theta}, s)$$

That is, the projection of the object in the case of multi-body motion may be equal to a sum of respective projections of all the units of the object. As t the object is moving during the CT scanning, CT projection at each angle corresponds to a different pattern of the object, so that it is impossible to perform a reconstruction by using the traditional CT reconstruction method. Or, the reconstruction will lead to a simple superposition of the respective different patterns of the object.

The embodiment of the present invention proposes a CT reconstruction method, which performs a matrix transformation on reconstructed images (its initial values are preset) of a scanned object with correspondence between the measured motions and the time moments when the motions occur. This is performed before a back projection of project data collected at different time moments, to make the images keep consistent with the object's patterns at each time moment. Thereafter, back-projection is performed; after data back-projection at the current time moment, the current image matrix is transformed into the object's pattern corresponding to a next time moment, and a back projection operation is further performed on a next set of projection data, until all project data have been subjected to back projection. Then, the current image matrix is transformed into a pattern at time t=0. As such, the CT reconstruction result of the object's pattern at time t=0 is obtained in which motion artifact is finally eliminated. Since motion parameters of the object at different time moments during the CT scanning have been measured, a reconstructed image of the object at any time moment may be obtained by performing an image matrix transformation using the reconstructed result at time t=0.

According to an embodiment of the present invention, each updated reconstructed image matrix may be transformed into a state at an initial time moment before each back projection operation.

Figure 5:
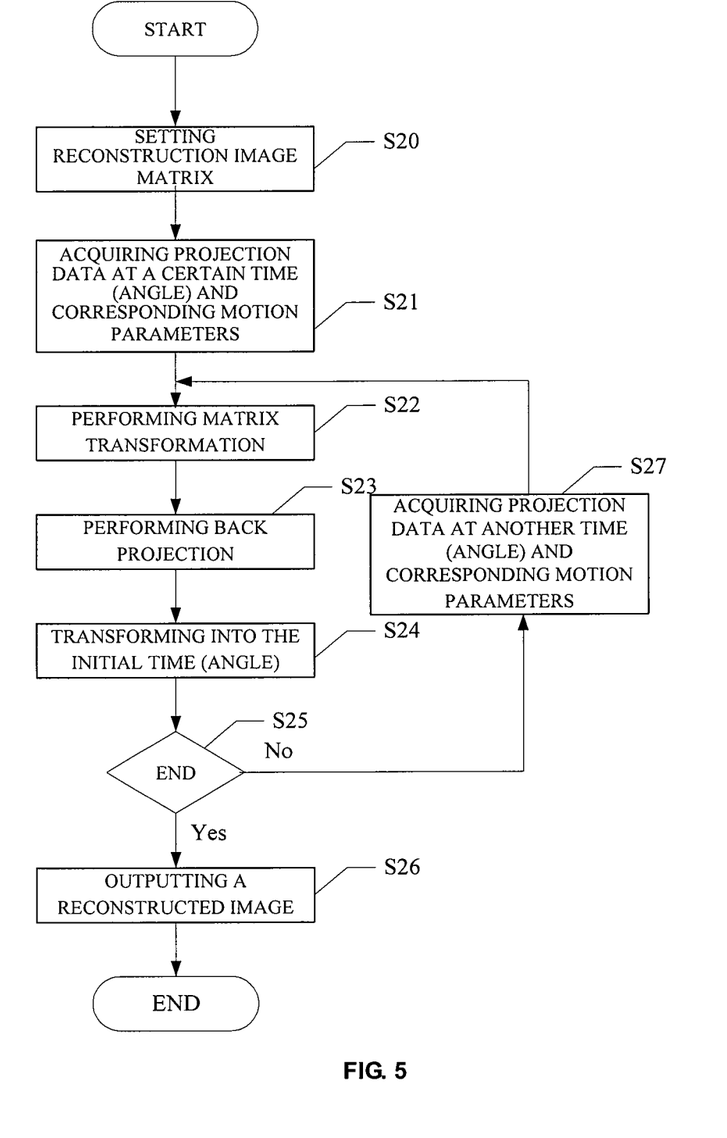
FIG. 5 shows a flowchart of an image reconstruction method according to an embodiment of the present invention.

FIG. 5 shows a flowchart of an image reconstruction process according to an embodiment of the present invention. As shown in FIG. 5, at step S20, all elements of a reconstructed image matrix of an object being scanned are set to zero or one, as an initial value for the image reconstruction matrix.

At step S21, projection data at a time moment (angle) and 3D motion parameters of the scanned object at this time moment are acquired.

At step S22, the computer 10 performs a matrix transformation on the above reconstructed image by using the 3D motion parameters to make the reconstructed image matrix consistent with the pattern of the object at the same time moment.

At step S23, the transformed reconstructed image matrix is updated by performing a back projection algorithm or other algorithms using the projection data.

At step S24, the updated reconstructed image matrix is transformed into the pattern at the initial time moment.

At step S25, it is determined whether the reconstruction shall end or not.

If the reconstruction shall end, a reconstructed image is outputted at step S26 for displaying on a display for example. As mentioned above, the reconstructed image at the initial time moment is acquired. Then, the reconstructed image at each time moment may be acquired by the matrix transformation.

If the reconstruction does not end, project data at another time moment (angle) and the corresponding 3D parameters are acquired at step S27. Then, the procedure proceeds to step S22, where the above operations will be repeated.

Hereinafter, the FBP algorithm and the ART (algebraic iteration) algorithm are taken as examples for detailed explanations of reconstruction process according to embodiments of the present invention.

1. Motion Compensation Algorithm of FBP Type:

For the FBP reconstruction equation (5), since projection data at different angles corresponds to different patterns of the object, they must be unified to enable accumulation of results of back projections at the respective angles. Equation (5) may be re-written as:

$$f(\vec{x}) = \int_{\theta} f_{FBP,\hat{\theta}}(\vec{x})d\hat{\theta} \qquad (11)$$

wherein:

$$f_{FBP,\hat{\theta}}(\vec{x}) = g(\hat{\theta},s)\delta(\hat{x}\cdot\hat{\theta}-s) \qquad (12)$$

For an object with multi-body motions, back projection of projection data at each angle corresponds to a pattern $f_t(\vec{x})$ of the object at a different time moment:

$$f_{FBP,t,\hat{\theta}}(\vec{x}) = g_t(\hat{\theta},s)\delta(\hat{x}\cdot\hat{\theta}-s) \qquad (13)$$

Therefore, the result of equation (13) can not be directly substituted into equation (11). Since 3D coordinates of the object corresponding to each projection angle and time have been obtained by calculation using the above stereo vision system, a rigid transformation equation for transforming the object from the time moment t to the time moment t=0 may be obtained:

$$f_{FBP,\hat{\theta}}(\vec{x}) = f_{FBP,t,\hat{\theta}}(\Gamma_t^{-1}(\vec{x})) \qquad (14)$$

wherein $\Gamma_t^{-1}$ is an inverse transformation for the rigid transformation equation (7). After substituting equation (14) into equation (11), the final FBP reconstruction equation with motion compensation may be obtained as:

$$f(\vec{x}) = \int_{\theta} f_{FBP,t=0,\hat{\theta}}(\vec{x})d\hat{\theta} \qquad (15)$$

2. Motion Compensation Algorithm of ART Type:

In addition to FBP algorithm, the ART algorithm is an iterative algorithm frequently applied in the practical CT system. Hereinafter, derivation is made as to how a reconstructed image matrix transformation is incorporated into the ART algorithm to get a new ART algorithm with motion compensation. The basic idea of the ART algorithm is to modify iterative images in accordance with a certain rule based on the projection value of each X-ray, and to finally obtain a reconstructed image with a convergence condition satisfied. Here, projection of the $j^{th}$ X-ray may be expressed as:

$$p_j = H_j f \qquad (16)$$

wherein $H_j$ is a projection matrix of this X-ray, and records contributions of the X-ray to all reconstruction matrix pixels that the X-ray passes. The calculation process of the new ART reconstruction algorithm is as follows:

(1) setting the initial iterative values for an image as $f_0^{k=0}$, the values usually being all zero or all one, that is, to set elements of the image transformation matrix to zero or 1;

(2) performing the $k^{th}$ iteration where the X-ray is projected as the $j^{th}$ projection value; this process can be divided into three sub-steps:

(2.1) transforming $f_0^k$ into a pattern at time t corresponding to the $j^{th}$ projection:

$$f_t^k(\vec{x}) = f_0^k(\Gamma_t^{-1}(\vec{x})) \quad (17)$$

(2.2) calculating and getting $f_t^{k+1}$ by substituting $f_t^k$ into the following equation:

$$\begin{cases} f_t^{k+1} = f_t^k + \dfrac{p_j - H_j f_t^k}{\|H_j\|^2} H_j^T & \|H_j\| \neq 0 \\ f_t^{k+1} = f_t^k & \|H_j\| = 0 \end{cases} \quad (18)$$

(2.3) transforming $f_t^{k+1}$ into an image matrix at time t=0:

$$f_0^k(\vec{x}) = f_t^k(\Gamma_t(\vec{x})) \quad (19)$$

(3) k=k+1, performing the next iteration, until the reconstructed image $f_0^k$ meets the convergence condition.

It shall be noted that the above reconstruction algorithm is not just limited to plane-beam CT, but may be easily extended to fan-beam and cone-beam CT image reconstruction. The following is experimental results of the above CT image reconstruction algorithm using computer simulation.

Figure 6:
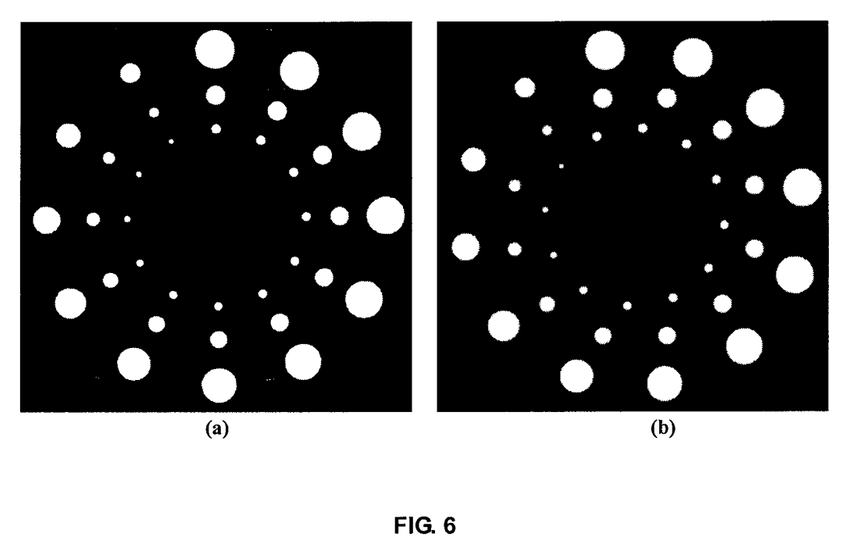
FIG. 6 shows a disk model used in testing a device and method according to an embodiment of the present invention, where

As shown in FIG. 6, a model containing 3 layers with a total of 36 discs is constructed. Each layer of discs has a different rotation speed. Linear attenuation sparse in the discs is set to 1, and for other parts, it is set to 0. FIG. 6 (a) shows an image of the model at the initial time, and FIG. 6(b) shows an image of the model which has be moving for a period of time.

Figure 7:
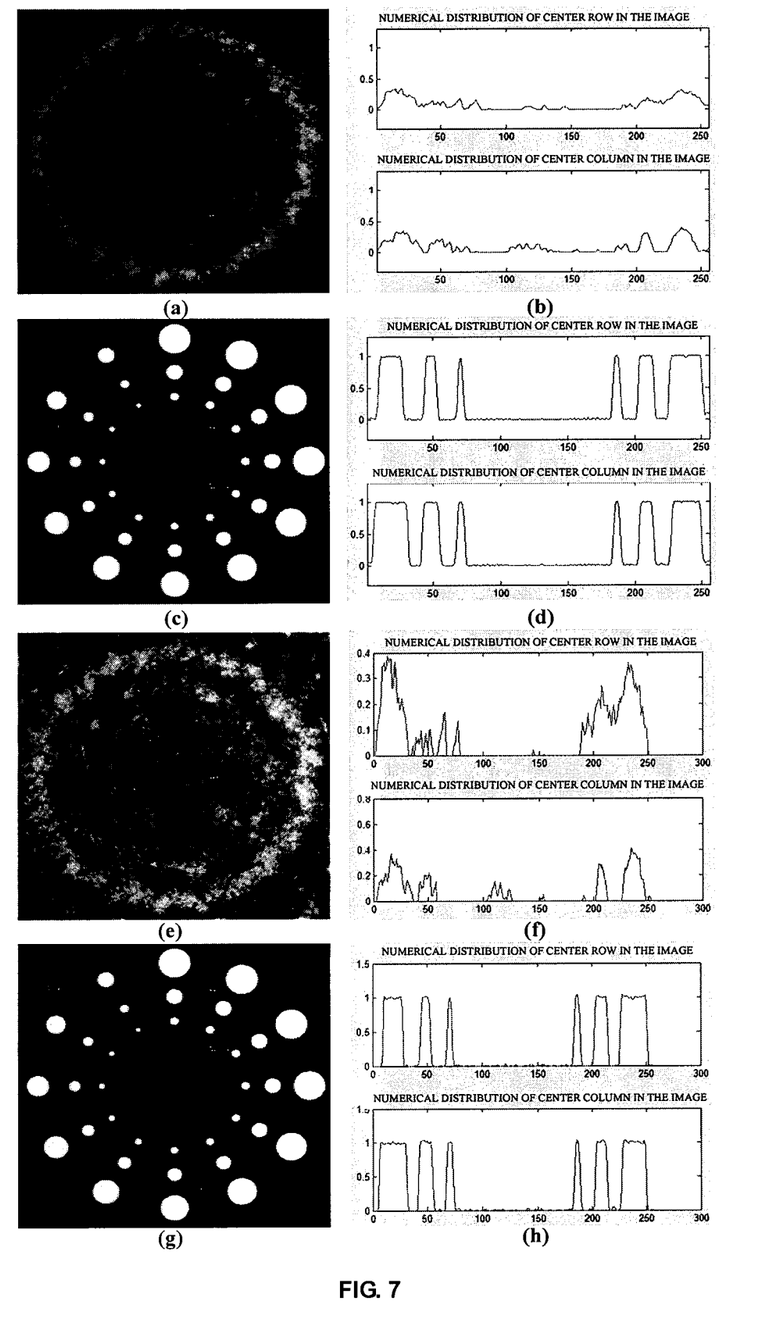
FIG. 7 shows simulated results obtained by performing a CT reconstruction on a moving object using a device according to an embodiment of the present invention, where

In the experiment, rotation speeds of the three disc layer are $2\omega_0$, $3\omega_0$ and $5\omega_0$, respectively, from outside toward inside. $\omega_0$ denotes the rotation scanning speed for the X-ray source and the detectors. Projections are collected for 260 out of 360 degrees. The number of the detectors is 256, and the number of pixels in the reconstructed image matrix is 256×256. FIG. 7 shows reconstruction results:

FIG. 7(a) is a result of performing a reconstruction directly using projection data of a moving object with the conventional FBP algorithm; it may be found that the respective discs are completely covered up by motion artifacts and cannot be distinguished;

FIG. 7(c) is a result of a new FBP reconstruction based on image matrix rotation of the present invention; it may be found that the image has been clearly reconstructed for all the discs, and the motion artifacts have been compensated;

FIGS. 7(b) and (d) are obtained along horizontal and vertical center section lines, respectively, in the reconstruction results of FIGS. 7(a) and (c); it may be found that the new motion-compensated FBP algorithm also brings in accurate reconstruction values;

FIG. 7(e) is a result of performing a reconstruction directly using project data of a moving object with the conventional ART algorithm; it may be found that all the discs are completely covered up by motion artifacts and cannot be distinguished;

FIG. 7(g) is a result of a new ART reconstruction based on image matrix rotation of the present invention; it may be found that the image has been clearly reconstructed for all the discs, and the motion artifacts have been compensated;

FIGS. 7(f) and (h) are obtained along horizontal and vertical center section lines, respectively, in the reconstruction results of Figs. (e) and (g); it may be found that the new motion-compensated ART algorithm also brings in accurate reconstruction values.

As noted above, the CT device and method using a stereo vision system according to the embodiments of the present invention are directed to eliminate motion artifacts in the CT images.

At present, CT technology has been applied in many technical fields. One of the problems frequently encountered in the CT applications is presence of some motions of an object during CT scanning process (especially in imaging a living object). This leads to reduction of image quality due to motion artifacts existing in CT images.

The hardware of the embodiments of the present invention can be easily embedded into the existing CT scanning equipments, thus allowing upgrade of system functions. The device and method according to the embodiments of the present invention substitute the object's 3D motion parameters, which are calculated through a stereo vision system, into the new motion-compensated FBP or ART algorithm, thereby effectively suppressing or even eliminating motion artifacts while improving quality of CT images. The device and method according to the embodiments of the present invention are important, especially for some special people groups that can not control their own motions, such as Parkinson's patients, infants, living mouse and so on. In addition, as for ultra-high-resolution CT imaging, even very slight motions might cause serious motion artifacts. In this case, the devices according to the embodiments of the invention are very useful.

The foregoing description is only intended to illustrate the embodiments of the present invention other than limiting the present invention. For those skilled in the art, any change or substitution that can be made readily within the scope of the present invention should be encompassed by the scope of the present invention. Therefore, the scope of the present invention should be defined by the claims.

What is claimed is:

1. A Computerized Tomography (CT) device based on motion compensation, comprising:

a CT scanning device adapted to perform CT scanning on a scanned object;

a stereo vision measurement system adapted to measure a motion parameter of the scanned object in synchronization with the scanning of the CT scanning device, wherein the stereo vision measurement system comprises a first camera and a second camera adapted to collect a 2D/3D image of the scanned object in synchronizations with the scanning of the CT scanning device, and wherein the synchronizations of the first and second cameras with the CT scanning device are based on collection timing of a detector in the CT scanning device; and an imaging device adapted to compensate for the motion of the scanned object during the CT scanning by performing a transformation on a reconstructed image matrix based on the motion parameter, wherein the imaging device is further configured to before a back-projection of projection data collected at different time moments, perform a matrix transformation on reconstructed images of a scanned object with correspondence between the measured motions and the time moments when the motions occur so as to make the images keep consistent with the object's patterns at each time moment;

perform a back-projection for the current set of image matrix;

after back-projection at the current moment, transform the current image matrix into the object's pattern corresponding to a next moment;

perform a back projection on a next set of projection data, until all projection data have been subjected to back projection; and transform the current image matrix into a pattern at initial moment;

wherein a period of a synchronous collection pulse trigger signal is adjusted to an integer multiple of a detector collection period, as collection triggers for the first and second cameras, when a detector collection rate used in the CT scanning device is higher than collection rates of the first and second cameras.

2. The CT device according to claim 1, wherein the imaging device calculates the motion parameter of the scanned object based on the collected 2D/3D image.

3. The CT device according to claim 1, wherein, when performing CT reconstruction, 3D coordinates and motion parameter of the scanned object are obtained in correspondence to CT projections by interpolation.

4. A Computerized Tomography device based on motion compensation, comprising:
  a CT scanning device adapted to perform CT scanning on a scanned object;
  a stereo vision measurement system adapted to measure a motion parameter of the scanned object in synchronization with the scanning of the CT scanning device, wherein the stereo vision measurement system comprises a first camera and a second camera adapted to collect a 2D/3D image of the scanned object in synchronizations with the scanning of the CT scanning device, and wherein the synchronizations of the first and second cameras with the CT scanning device are based on collection timing of a detector in the CT scanning device; and
  an imaging device adapted to compensate for the motion of the scanned object during the CT scanning by performing a transformation on a reconstructed image matrix based on the motion parameter, wherein the imaging device is further configured to:
    before a back-projection of projection data collected at different time moments, perform a matrix transformation on reconstructed images of a scanned object with correspondence between the measured motions and the time moments when the motions occur so as to make the images keep consistent with the object's patterns at each time moment;
    perform a back-projection for the current set of image matrix;
    after back-projection at the current moment, transform the current image matrix into the object's pattern corresponding to a next moment;
    perform a back projection on a next set of projection data, until all projection data have been subjected to back projection; and
    transform the current image matrix into a pattern at initial moment;
  wherein a detector collection signal is used as a synchronous trigger signal for the first and second cameras for image collection, when a detector collection rate used in the CT scanning device is lower than collection rates of the first and second cameras.

5. The CT device according to claim 1, wherein the motion parameter includes at least a part of rotation and translation of the scanned object.

6. The CT device according to claim 1, wherein the compensation for the motion is implemented in Filtered-Back Projection (FBP) and Algebraic Reconstruction Technique (ART) algorithms.

7. A method for use in a Computerized Tomography (CT) device, comprising:
  performing CT scanning on a scanned object with a CT scanning device;
  measuring a motion parameter of the scanned object in synchronization with the scanning of the CT scanning device; and
  compensating for the motion of the scanned object during the CT scanning by performing a transformation on a reconstructed image matrix based on the motion parameter, wherein the compensating comprises
    before a back-projection of projection data collected at different time moments, performing a matrix transformation on reconstructed images of a scanned object with correspondence between the measured motions and the time moments when the motions occur so as to make the images keep consistent with the object's patterns at each time moment;
    performing a back-projection for the current set of image matrix;
    after back-projection at the current moment, transforming the current image matrix into the object's pattern corresponding to a next moment;
    performing a back projection on a next set of projection data, until all project data have been subjected to back projection; and
    transforming the current image matrix into a pattern at initial moment,
  wherein a 2D/3D image of the scanned object is collected in synchronization with the scanning of the CT scanning device through a first and a second cameras, and the motion parameter of the scanned object is calculated based on the collected 2D/3D image,
  wherein the synchronizations of the first and second cameras with the CT scanning device are based on collection timing of a detector in the CT scanning device, and
  wherein a period of a synchronous collection pulse trigger signal is adjusted to an integer multiple of a detector collection period, as collection triggers for the first and second cameras, when a detector collection rate used in the CT scanning device is higher than collection rates of the first and second cameras.

8. The method according to claim 7, wherein, when performing CT reconstruction, 3D coordinates and the motion parameter of the scanned object are obtained in correspondence to CT projections by interpolation.

9. A method for use in a Computerized Tomography (CT) device, comprising:
  performing CT scanning on a scanned object with a CT scanning device;
  measuring a motion parameter of the scanned object in synchronization with the scanning of the CT scanning device; and
  compensating for the motion of the scanned object during the CT scanning by performing a transformation on a reconstructed image matrix based on the motion parameter, wherein the compensating comprises:
    before a back-projection of projection data collected at different time moments, performing a matrix transformation on reconstructed images of a scanned object with correspondence between the measured motions and the time moments when the motions occur so as to make the images keep consistent with the object's patterns at each time moment;
    performing a back-projection for the current set of image matrix;

after back-projection at the current moment, transforming the current image matrix into the object's pattern corresponding to a next moment;

performing a back projection on a next set of projection data, until all projection data have been subjected to back projection; and transforming the current image matrix into a pattern at initial moment, wherein a 2D/3D image of the scanned object is collected in synchronization with the scanning of the CT scanning device through a first and a second cameras, and the motion parameter of the scanned object is calculated based on the collected 2D/3D image, wherein the synchronizations of the first and second cameras with the CT scanning device are based on collection timing of a detector in the CT scanning device, wherein a period of a synchronous collection pulse trigger signal is adjusted to an integer multiple of a detector collection period, as collection triggers for the first and second cameras, when a detector collection rate used in the CT scanning device is higher than collection rates of the first and second cameras, and wherein a detector collection signal is used as a synchronous trigger signal for the first and second cameras for image collection, when the detector collection rate used in the CT scanning device is lower than the collection rates of the first and second cameras.

10. The method according to claim 7, wherein the motion parameter includes at least a part of rotation and translation of the scanned object.

11. The method according to claim 7, wherein the compensation for the motion is implemented in Filtered-Back Projection (FBP) and Algebraic Reconstruction Technique (ART) algorithms.

* * * * *